US007732142B2

(12) United States Patent
Ebersole et al.

(10) Patent No.: US 7,732,142 B2
(45) Date of Patent: Jun. 8, 2010

(54) SEQUENCES DIAGNOSTIC FOR SHRIMP PATHOGENS

(75) Inventors: Richard C. Ebersole, Wilmington, DE (US); Jianzhong Zhang, Wilmington, DE (US); Christian Peter Lenges, Wilmington, DE (US); Mario W. Chen, Chadds Ford, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/840,261

(22) Filed: Aug. 17, 2007

(65) Prior Publication Data

US 2008/0293037 A1 Nov. 27, 2008

Related U.S. Application Data

(60) Provisional application No. 60/839,865, filed on Aug. 24, 2006.

(51) Int. Cl.
*C12Q 1/68* (2006.01)
*C07H 21/02* (2006.01)

(52) U.S. Cl. .......................... 435/6; 536/23.1
(58) Field of Classification Search ........................ None
See application file for complete search history.

(56) References Cited

U.S. PATENT DOCUMENTS

| 4,683,195 | A | 7/1987 | Mullis et al. |
| 4,683,202 | A | 7/1987 | Mullis et al. |
| 5,994,056 | A | 11/1999 | Higuchi |
| 6,190,862 | B1 | 2/2001 | Kou et al. |
| 6,582,908 | B2 * | 6/2003 | Fodor et al. ............... 506/9 |

FOREIGN PATENT DOCUMENTS

CN 1410549 4/2003

OTHER PUBLICATIONS

GENBANK Accession No. 218266.*
Buck et al. ("Design Strategies and Performance of Custom DNA Sequencing Primers") BioTechniques. Sep. 1999. 27: pp. 528-536).*
Dhar et al. (J Clin Microbiol. Aug. 2001;39(8):2835-45).*
Stratagene ("Gene Characterization Kits" 1988).*
New England Biolabs 1998/99 Catalog (NEB Catalog).*
Tang et al., Detection and Quantification of Infectious Hypodermal and Hematopoietic Necrosis Virus in Penaeid Shrimp by Real-Time PCR, Diseases of Aquatic Organisms, 2001, pp. 79-85, vol. 44.
Nunan et al., Use of Polymerase Chain Reaction for the Detection of Infectious Hypodermal and Hematopoietic Necrosis Virus in Penaeid Shrimp, Marine Biotechnology, 2000, pp. 319-328, vol. 2.
Tabor et al., A Bacteriophage T7 RNA Polymerase/Promoter System for Controlled Exclusive Expression of Specific Genes, Proceedings of the National Academy of Sciences of the U.S., 1985, pp. 1074-1078, vol. 82.

Walker et al., Isothermal in Vitro Amplification of DNA by a Restriction Enzyme/DNA Polymerase System, Proceedings of the National Academy of Sciences of the U.S., 1992, pp. 392-396, vol. 89.
Sun et al., Sensitive and Rapid Detection of Infectious Hypodermal and Hematopoietic Necrosis Virus (IHHNV) in Shrimps by Loop-Mediated Isothermal Amplification, Journal of Virological Methods, 2006, pp. 41-46, vol. 131.
Dhar et al., Detection and Quantification of Infectious Hypodermal and Hematopoietic Necrosis Virus and White Spot Virus in Shrimp Using Real-Time Quantitative PCR and SYBR Green Chemistry, Journal of Clinical Microbiology, 2001, pp. 2835-2845, vol. 39 (8).
Yoganandhan et al., A Rapid Non-Enzymatic Method of DNA Extraction for PCR Detection of White Spot Syndrome Virus in Shrimp, Aquaculture Research, 2003, pp. 1093-1097, vol. 34.
Goel et al., A Review: Molecular Beacon: A Multitask Probe, Journal of Applied Microbiology, 2005, pp. 435-442, vol. 99.
Lightner et al., Shrimp Diseases and Current Diagnostic Methods, Aquaculture, 1998, pp. 201-220, vol. 164.
Sanger et al., DNA Sequencing With Chain-Terminating Inhibitors, Proceedings of the National Academy of Sciences of the U.S., 1977, pp. 5463-5467, vol. 74 (12).
Yue et al., Development of Real-Time Polymerase Chain Reaction Assay With Taqman Probe for the Quantitative Detection of Infectious Hypodermal and Hematopoietic Necrosis Virus From Shrimp, Journal of AOAC International, 2006, pp. 240-244, vol. 89 (1).
Van Necs et al., The Use of Oligodeoxynucleotide Probes in Chaotrope-Based Hybridization Solutions, Nucleic Acids Research, 1991, pp. 5143-5151, vol. 19 (19).
Yang et al., A Single-Step Multiplex PCR for Simultaneous Detection of White Spot Syndrome Virus and Infectious Hypodermal and Haematopoietic Necrosis Virus in Penaeid Shrimp, Journal of Fish Diseases, 2006, pp. 301-305, vol. 29.
Shike et al., Infectious Hypodermal and Hematopoietic Necrosis Virus of Shrimp is Related to Mosquito Brevidensoviruses, Virology, 2000, pp. 167-177, vol. 277.
Bonami et al., Purification and Characterization of the Infectious Hypodermal and Haematopoietic Necrosis Virus of Penaeid Shrimps, Journal of General Virology, 1990, pp. 2657-2664, vol. 71 (11).
Sambrook et al., Molecular Cloning: A Laboratory Manual, 2nd Edition, 1989, Cold Spring Harbor Press, Cold Spring Harbor, NY (Book Not Included).
Ausubel et al., Current Protocols in Molecular Biology, 1987, Greene Publishing Assoc. and Wiley Interscience (Book Not Included).
Silhavy et al., Experiments With Gene Fusions, 1984, Cold Spring Harbor Laboratory Press, Cold Spring Harbor, NY (Book Not Included).
International Search Report Dated Feb. 11, 2008 for International Application No. PCT/US2007/018344 (4 pages).
International Preliminary Report on Patentability in related PCT/US2007/018344 mailed Mar. 5, 2009.

* cited by examiner

*Primary Examiner*—Christopher M. Babic

(57) ABSTRACT

Primers have been isolated that are diagnostic for the detection of the infectious hypodermal and hematopoietic necorsis virus (IHHNV). The primers are based on a new portion of the IHHNV genome and may be used in primer directed amplification or nucleic acid hybridization assay methods.

28 Claims, 1 Drawing Sheet

SEQUENCES DIAGNOSTIC FOR SHRIMP PATHOGENS

CROSS-REFERENCE TO RELATED APPLICATION

This application claims priority under 35 U.S.C. §119 from U.S. Provisional Application Ser. No. 60/839,865, filed Aug. 24, 2006.

FIELD OF THE INVENTION

The invention relates to the field of diagnostic testing. More specifically, new primers have been developed for use in detection of the Infectious Hypodermal and Hematopoietic Necrosis Virus pathogen of shrimp.

BACKGROUND OF THE INVENTION

Commercial shrimp farms suffer extensive losses due to the effects of a number of common pathogens. Infectious Hypodermal and Hematopoietic Necrosis Virus (IHHNV) is one of the most serious viral pathogens of farmed penaeid shrimp. It is widely distributed in many countries and has a large range of hosts. For example, IHHNV causes mass mortality among the Western blue shrimp (*Penaeus stylirostris*) and severe deformation in the Pacific white shrimp (*Penaeus vannamei*). IHHNV is a small, single stranded DNA-containing parvovirus, the complete genome of which has been sequenced (Bonami et al., *J. Gen. Virology* 71 (Pt 11):657-2664 (1990); GenBank AF218266).

IHHNV is extremely detrimental to the shrimp farming industry, being responsible for catastrophic epidemics worldwide. Detection of IHHNV in hatchery broodstock and in post-larvae allows infected shrimp to be eliminated before entry into a commercial production system. Consequently, a variety of methods have been developed for the detection of IHHNV in shrimp, including nucleic acid-based methods and immunological methods (Lightner et al., *Aquaculture* 164(1): 201-220 (1998)). Nucleic acid amplification methods such as polymerase chain reaction (PCR) and isothermal amplification are of particular interest because they are simple, rapid, and sensitive. PCR methods for the detection of IHHNV, which are based on amplifying different diagnostic regions of the genome, have been described (see for example Nunan et al., *Mar. Biotechnol.* 2(4):319-328 (2000); Yue et al., *J. AOAC International* 89(1):240-244 (2006); Tang et al. *Dis. Aquat. Org.* 44(2):79-85 (2001); Hu et al., CN 1410549; and Dhar et al. *J. Clin. Microbiol.* 39(8):2835-2845 (2001)). Additionally, a loop mediated isothermal method for the detection of IHHNV is described by Sun et al. (*J. Virol. Methods* 131(1): 41-46 (2006)).

All of the above methods are useful for the detection of IHHNV; however, they generally suffer from a lack of specificity, sensitivity, or are complex and time consuming. Additionally, because of the high gene mutation rate in the virus, tests directed to different regions of the genome would be useful. Therefore, there is a need for a highly sensitive assay for IHHNV that is rapid, accurate and easily used in the field. The stated problem is addressed herein by the discovery of primers based on new portions of the IHHNV genome. The primers identified herein can be used in primer directed amplification or nucleic acid hybridization assay methods for the detection of IHHNV without the problems associated with previous methodologies.

SUMMARY OF THE INVENTION

In one embodiment, the present invention provides an isolated IHHNV diagnostic primer sequence as set forth in any one of SEQ ID NOs:1-8 or an isolated nucleic acid molecule that is completely complementary to SEQ ID NOs:1-8.

In another embodiment, the invention provides a pair of two different IHHNV diagnostic primer sequences as disclosed herein, wherein the pair is capable of priming a nucleic acid amplification reaction that amplifies a region of nucleic acid within the IHHNV genome.

In another embodiment, the invention provides a kit for the detection of IHHNV comprising at least one pair of IHHNV diagnostic primer sequences disclosed herein.

In another embodiment, the invention provides a method for detecting the presence of IHHNV in a sample comprising:
  (i) providing DNA from a sample suspected of containing the IHHNV; and
  (ii) probing the DNA with a probe derived from the isolated IHHNV diagnostic primer sequence of any of SEQ ID NOs:1-8 under suitable hybridization conditions;
  wherein the identification of a hybridizable nucleic acid fragment confirms the presence of IHHNV.

In other embodiments the detection methods identify DNA samples that are not infected with IHHNV.

In another embodiment, the invention provides a method for detecting the presence of IHHNV in a sample comprising:
  (i) providing DNA from a sample suspected of containing IHHNV; and
  (ii) amplifying the DNA with at least one pair of IHHNV diagnostic primer sequences disclosed herein such that amplification products are generated;
  wherein the presence of amplification products confirms the presence of IHHNV.

In another embodiment, the invention provides a method for quantifying the amount of IHHNV in a sample comprising:
  (i) providing DNA from a sample suspected of containing IHHNV;
  (ii) amplifying the DNA with at least one pair of IHHNV diagnostic primer sequences disclosed herein by thermal cycling between at least a denaturing temperature and an extension temperature in the presence of a nucleic acid-binding fluorescent agent or a fluorescently labeled probe;
  (iii) measuring the amount of fluorescence generated by the nucleic acid-binding fluorescent agent or the fluorescently labeled probe during the thermal cycling;
  (iv) determining a cycle threshold number at which the amount of fluorescence generated by the nucleic acid-binding fluorescent agent or the fluorescently labeled probe reaches a fixed threshold value above a baseline value; and
  (v) calculating the amount of IHHNV in the sample by comparing the cycle threshold number determined for the IHHNV in the sample with a standard curve of the cycle threshold number versus the logarithm of template concentration determined using standard solutions of known concentration.

BRIEF DESCRIPTION OF THE FIGURE AND SEQUENCE DESCRIPTIONS

The various embodiments of the invention can be more fully understood from the following detailed description and the accompanying sequence descriptions, which form a part of this application.

Figure 1:
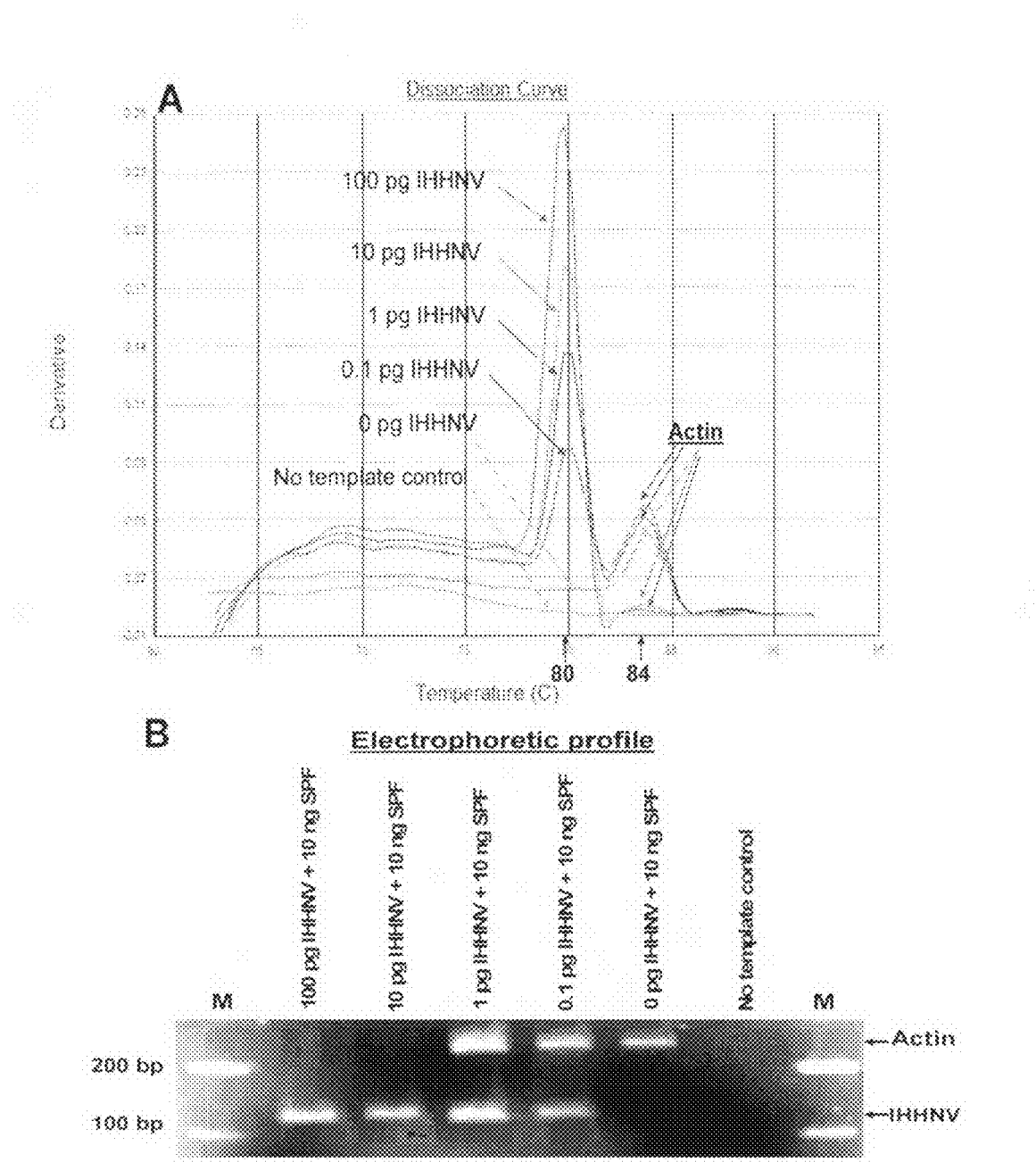
FIG. 1A shows the melting curve for the IHHNV4 product and the actin internal sample control product formed by simultaneous PCR amplification of the IHHNV virus DNA and actin DNA, as described in Example 10. The melting temperature (Tm) values of the IHHNV and actin products are indicated on their corresponding melting curves.
FIG. 1B shows the results of the agarose gel electrophoresis separation of samples containing the IHHNV4 product and the actin internal sample control product formed by simultaneous PCR amplification of the IHHNV virus DNA and actin DNA, as described in Example 10. The quantity of IHHNV and shrimp DNA is shown above each lane; "M" is a 100-bp DNA ladder.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-8 are the nucleotide sequences of IHHNV diagnostic primers useful for detection of IHHNV.

SEQ ID NOs:9-12 are the nucleotide sequences of synthetic IHHNV templates described in the General Methods Section of the Examples. These sequences are also the nucleotide sequences of amplification products obtained using pairs of IHHNV diagnostic primers disclosed herein.

SEQ ID NOs:13-16 are the nucleotide sequences of internal sample control primers described in Example 10.

SEQ ID NOs:17 and 18 are the nucleotide sequences of fluorescently labeled probes.

DETAILED DESCRIPTION OF THE INVENTION

Disclosed herein are primers useful in assays for the detection of infectious hypodermal and hematopoietic necorsis virus (IHHNV). The primers may be used in nucleic acid amplification methods as well as in hybridization assays for the efficient detection and quantification of virulent infectious hypodermal and hematopoietic necorsis virus.

In this disclosure, a number of terms and abbreviations are used. The following definitions are provided and should be referred to for interpretation of the claims and the specification.

"Polymerase chain reaction" is abbreviated PCR.

"Infectious Hypodermal and Hematopoietic Necorsis Virus" is abbreviated IHHNV.

The term "isolated IHHNV diagnostic primer sequence" refers to a sequence corresponding to a portion of the IHHNV genome being diagnostic for the presence of IHHNV.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "amplification product" or "amplicon" refers to the nucleic acid fragment that is produced during a primer directed amplification reaction. Typical methods of primer directed amplification include polymerase chain reaction (PCR), ligase chain reaction (LCR), strand displacement amplification (SDA), or other isothermal amplification processes. If PCR methodology is selected, the replication composition would typically include, for example: deoxynucleotide triphosphates, two primers with appropriate sequences, a thermostable DNA polymerase and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions would comprise, for example: a thermostable ligase (e.g., *T. aquaticus* ligase), two sets of adjacent oligonucleotides (wherein one member of each set is complementary to each of the target strands), Tris-HCl buffer, KCl, EDTA, NAD, dithiothreitol and salmon sperm DNA (see for example, Tabor et al., *Proc. Natl. Acad. Sci. U.S.A.,* 82:1074-1078 (1985)).

The term "primer" refers to an oligonucleotide (synthetic or occurring naturally), which is capable of acting as a point of initiation of nucleic acid synthesis or replication along a complementary strand when placed under conditions in which synthesis of a complementary stand is catalyzed by a polymerase.

The term "thermal cycling" refers to the entire pattern of changing temperature used during certain nucleic acid amplification methods, such as PCR and LCR. This process is common and well known in the art. See, for example, Sambrook, J., Fritsch, E. F. and Maniatis, T., *Molecular Cloning: A Laboratory Manual,* $2^{nd}$ ed., Cold Spring Harbor Laboratory Press: Cold Spring Harbor, N.Y. (1989); and U.S. Pat. No. 4,683,202 to Mullis et al. and U.S. Pat. No. 4,683,195 to Mullis et al. In general, PCR thermal cycling includes an initial denaturing step at high temperature, followed by a repetitive series of temperature cycles designed to allow template denaturation, primer annealing, and extension of the annealed primers by the polymerase.

The term "cycle threshold number", also referred to herein as "CT", refers to the cycle number during thermal cycling at which the amount of fluorescence due to product formation reaches a fixed threshold value above a baseline value.

The term "probe" refers to an oligonucleotide (synthetic or occurring naturally) that is significantly complementary to a target sequence, also referred to herein as a "fragment", (i.e., the sequence to be detected or a portion of the sequence to be detected) and forms a duplexed structure by hybridization with at least one strand of the target sequence. The probe can be labeled to facilitate detection, for example, using a fluorescent label or a ligand label.

The term "replication inhibitor moiety" refers to any atom, molecule or chemical group that is attached to the 3' terminal hydroxyl group of an oligonucleotide that will block the initiation of chain extension for replication of a nucleic acid strand. Examples include, but are not limited to, 3' deoxynucleotides (e.g., cordycepin), dideoxynucleotides, phosphate, ligands (e.g., biotin and dinitrophenol), reporter molecules (e.g., fluorescein and rhodamine), carbon chains (e.g., propanol), a mismatched nucleotide or polynucleotide, or peptide nucleic acid units.

The term "non-participatory" refers to the lack of participation of a probe or primer in a reaction for the amplification of a nucleic acid molecule. Specifically, a non-participatory probe or primer is one that will not serve as a substrate for, or be extended by, a DNA polymerase. A "non-participatory probe" is inherently incapable of being chain extended by a polymerase. It may or may not have a replication inhibitor moiety.

A nucleic acid molecule is "hybridizable" to another nucleic acid molecule, such as a cDNA, genomic DNA, or RNA, when a single stranded form of the nucleic acid molecule can anneal to the other nucleic acid molecule under suitable conditions of temperature and solution ionic strength. Hybridization and washing conditions are well known and exemplified in Sambrook, J., Fritsch, E. F. and Maniatis, T. *Molecular Cloning: A Laboratory Manual,* 2nd ed., Cold Spring Harbor Laboratory Press: Cold Spring Harbor, N.Y. (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a melting temperature (Tm) of 55° C., can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment, the length for a hybridizable nucleic acid is at least about 10 nucleotides. Preferably, a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), DNASTAR (DNASTAR, Inc., Madison, Wis.), and Vector NTI® software version 7.0. Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual,* $2^{nd}$ ed., Cold Spring Harbor Laboratory Press: Cold Spring Harbor, N.Y. (1989) (hereinafter "Maniatis"); and by Ausubel, F. M. et al., *Current Protocols in Molecular Biology,* published by Greene Publishing Assoc. and Wiley-Interscience (1987).

Infectious Hypodermal and Hematopoietic Necorsis Virus Genome

The infectious hypodermal and hematopoietic necorsis virus (IHHNV) is a major shrimp pathogen with a high mortality rate and a broad host range. The complete genome of IHHNV has been sequenced (Bonami et al., *J. Gen. Virology* 71 (Pt 11):657-2664 (1990); GenBank AF218266). The genome consists of single stranded DNA containing 4,075 bases and 3 open reading frames (ORFs).

IHHNV Diagnostic Primer Sequences

Disclosed herein are diagnostic primer sequences useful in a variety of assay formats for high sensitive detection of IHHNV. These primers are directed to regions of the IHHNV genome not previously used for IHHNV detection.

Primer sequences were empirically identified using a series of "in silica" (i.e., computer-based) sequence analysis tools. In this process, a database was assembled containing all known IHHNV sequences. These sequences were first aligned and then analyzed for primer sites using Vector NTI® software (InforMax Inc., Bethesda, Md.) based on homology with other IHHNV sequences, a specified amplicon length, salt concentration, Tm (melting temperature), C+G content and freedom from hairpin and secondary structure parameters. Prospective primers were then screened against GenBank sequences. Those primers established to contain less than 5 bases of homology with other non-target gene sequences were selected for experimental investigation of PCR amplification efficiency and minimal primer-dimer formation. Primers showing both high amplification efficiency and minimal primer-dimer formation were selected for testing with a panel of DNA isolated from shrimp infected with various shrimp pathogens and DNA from shrimp certified to be disease-free. Those primers amplifying all IHHNV strains and showing no response to both DNA from shrimp infected with non-IHHNV pathogens and to DNA isolated from different species of certified disease free shrimp were selected as useful primers.

The primer sequences found to be useful in the detection of IHHNV and their location in the IHHNV genome are given in Table 1. These primers may be synthesized using standard phosphoramidite chemistry or may be purchased from companies such as Sigma Genosys (The Woodlands, Tex.).

TABLE 1

IHHNV Diagnostic Primer Sequences

| Primer, Direction | SEQ ID NO: | IHHNV Genome Location (GenBank AF218266) |
|---|---|---|
| IHHNV1F, Forward | 1 | 682-705 |
| IHHNV1R, Reverse | 2 | 779-800 |
| IHHNV2F, Forward | 3 | 1062-1086 |
| IHHNV2R, Reverse | 4 | 1137-1161 |
| IHHNV3F, Forward | 5 | 1749-1773 |
| IHHNV3R, Reverse | 6 | 1832-1856 |
| IHHNV4F, Forward | 7 | 3417-3440 |
| IHHNV4R, Reverse | 8 | 3508-3532 |

Assay Methods

The primer sequences disclosed herein may be used in a variety of assay formats for the detection and quantification of IHHNV. The two most convenient formats rely on methods of nucleic acid hybridization or primer directed amplification methods such as PCR.

Primer Directed Amplification Assay Methods

In one embodiment, the present IHHNV diagnostic primer sequences may be used in primer directed nucleic acid amplification for the detection of the presence of IHHNV. A variety of primer directed nucleic acid amplification methods are well known in the art and are suitable for use with the primers disclosed herein. These nucleic acid amplification methods include thermal cycling methods (e.g., polymerase chain reaction (PCR) and ligase chain reaction (LCR)), as well as isothermal methods and strand displacement amplification (SDA).

LCR methods are well known in the art (see for example, Tabor et al., *Proc. Natl. Acad. Sci. U.S.A.*, 82:1074-1078 (1985)). Typically, LCR nucleic acid replication compositions comprise, for example: a thermostable ligase (e.g., *T. aquaticus* ligase), two sets of adjacent oligonucleotide primers (wherein one member of each set is complementary to each of the target strands), Tris-HCl buffer, KCl, EDTA, NAD, dithiothreitol and salmon sperm DNA.

SDA methods are also well known in the art. An in depth discussion of SDA methodology is given by Walker et al. (*Proc. Natl. Acad. Sci. U.S.A.*, 89:392 (1992)). Typically in SDA, two oligonucleotide primers are used, each having regions complementary to only one of the stands in the target. After heat denaturation, the single-stranded target fragments bind to the respective primers which are present in excess. Both primers contain asymmetric restriction enzyme recognition sequences located 5' to the target binding sequences. Each primer-target complex cycles through nicking and polymerization/displacement steps in the presence of a restriction enzyme, a DNA polymerase and three deoxynucleotide triphosphates (dNTPs) and one deoxynucleotide α-thio triphosphate (dNTP[aS]).

The preferred method for detecting IHHNV using the diagnostic primer sequences disclosed herein is PCR, which is described by Mullis et al. in U.S. Pat. No. 4,683,202 and U.S. Pat. No. 4,683,195, which are both specifically incorporated herein by reference. In PCR methods, the IHHNV diagnostic primer sequences disclosed herein and their complete complementary sequences are used in pairs which are capable of priming a nucleic acid amplification reaction that amplifies a region within the IHHNV genome. Various combinations of the IHHNV diagnostic primer sequences and their complements can be used. Suitable primer pairs include, but are not limited to, SEQ ID NOs:1 and 2, SEQ ID NOs:3 and 4, SEQ ID NOs:5 and 6, SEQ ID NOs:7 and 8, and SEQ ID NOs:1 and 4.

Generally, the two primers are mixed with the sample DNA, a mixture of four deoxynucleotide triphosphates (i.e., dATP, dCTP, dTTP, and dGTP), a thermostable DNA polymerase, such as Taq DNA polymerase, in a buffer solution. This mixture is then thermal cycled using a thermal cycler instrument to amplify the desired target region. Thermal cyclers are commercially available from many sources (e.g., Applied Biosystems (Foster City, Calif.); Brinkmann (Westbury, N.Y.); MJ Research (Waltham, Mass.); and Stratagene (La Jolla, Calif.)).

In general, PCR thermal cycling includes an initial denaturing step at high temperature, followed by a repetitive series of temperature cycles designed to allow template denaturation, primer annealing, and extension of the annealed primers by the polymerase. Generally, the samples are heated initially for about 2 to 10 minutes at a temperature of about 95° C. to denature the double stranded DNA sample. Then, in the beginning of each cycle, the samples are denatured for about 10 to 60 seconds, depending on the samples and the type of instrument used. After denaturing, the primers are allowed to anneal to the target DNA at a lower temperature, from about 40° C. to about 60° C. for about 20 to 60 seconds. Extension of the primers by the polymerase is often carried out at a temperature ranging from about 60° C. to about 72° C. The amount of time used for extension will depend on the size of the amplicon and the type of enzymes used for amplification and is readily determined by routine experimentation. Additionally, the annealing step can be combined with the extension step, resulting in a two step cycling. Thermal cycling may also include additional temperature shifts in PCR assays. The number of cycles used in the assay depends on many factors, including the primers used, the amount of sample DNA present, and the thermal cycling conditions. The number of cycles to be used in any assay may be readily determined by one skilled in the art using routine experimentation. Optionally, a final extension step may be added after the completion of thermal cycling to ensure synthesis of all amplification products.

Following amplification, the amplified nucleotide sequence may be ligated to a suitable vector followed by transformation of a suitable host organism with said vector. One thereby ensures a more readily available supply of the amplified sequence. Alternatively, following amplification, the amplified sequence or a portion thereof may be chemically synthesized for use as a nucleotide probe for use in a hybridization assay, as described below. In either situation the DNA sequence of the variable region may be established using methods such as the dideoxy method (Sanger, F. et al. *Proc. Natl. Acad. Sci.* 74:5463-5467 (1977)). The sequence obtained is used to guide the choice of the probe for the organism and the most appropriate sequence(s) is/are selected.

In order to detect the presence of IHHNV in a sample suspected of containing IHHNV (e.g., shrimp or other crustaceans) using a primer directed nucleic acid amplification method, DNA from the sample must be provided in a form that is capable of being amplified. Typically, the DNA must be free from the cell and sample materials and may be treated to eliminate proteins and other cell components. The DNA may be obtained from any suitable tissue, fluid or sample material including, but not limited to, shrimp tissue (e.g., gills, pleopods, hemolymph, muscle, tail, eyestalk, stomach, leg, and connective tissue), wash fluids, and pond water samples. The samples may be suspected of containing IHHNV for any number of reasons, including proximity to a known contaminant or otherwise, or may only be suspected of contamination by virtue of IHHNV's common presence in the commercial shrimp industry. Thus, a sample suspected of containing IHHNV can be any DNA sample described above.

Methods for providing DNA, which is suitable for amplification, from tissues are well known in the art. For example, DNA may be extracted from a sample by homogenizing the sample material or tissue in Tris-HCl buffer containing NaCl, centrifuging to remove solid debris, and using the resulting supernatant fluid in the PCR reaction, as described by Nunan et al. (*Mar. Biotechnol.* 2(4):319-328 (2000)). Alternatively, the methods for isolating white spot syndrome viral DNA from various tissues described by Yoganandhan et al. (*Aquaculture Research* 34(12):1093-1097 (2003)) and Kou et al. (U.S. Pat. No. 6,190,862) may be used. The DNA may also be provided in a form which is suitable for amplification using a commercially available DNA isolation kit, such as the QIAamp DNA Mini Kit (Qiagen, Valencia Calif.), or DNAzol® Genomic DNA Isolation Reagent (Molecular Research Center, Inc., Cincinnati, Ohio).

The DNA is then amplified with at least one pair of diagnostic primer sequences disclosed herein using a nucleic acid amplification method, as described above. A combination of different pairs of diagnostic primer sequences may also be used. The presence of the amplification product, detected as described below, confirms the presence of IHHNV in the sample. In one embodiment, PCR is used to amplify the DNA.

In nucleic acid amplification methods, test results can be misinterpreted due to reagent failure, procedural errors, and instrument malfunction. Additionally, problems arise due to the presence of inhibitory substances in the sample materials or degradation of the sample DNA or RNA during sample processing and nucleic acid recovery. To overcome these problems, internal control tests can be performed in combination with the IHHNV assay to alert users to these types of errors and to aid in quantification of test results.

Two types of internal control tests can be used. One approach is based on co-amplification of an "internal template control" (ITC), which is added to the nucleic acid amplification reagent mixture prior to reaction. A second approach is based on co-amplification of an "internal sample control" (ISC) contained in the sample. In both cases, the sequence of the internal control DNA or RNA is different from that of the IHHNV DNA.

The internal sample control can be a DNA or RNA gene sequence conserved or consistently present in sample materials (e.g. shrimp tissue and hemolymph). The primers used to amplify the ISC target DNA or RNA are chosen so that they do not amplify IHHNV DNA and the IHHNV test primers are chosen so that they do not amplify the internal sample control DNA or RNA targets. In this way, the ISC and IHHNV targets amplify independently. In the assay, both the ISC and the IHHNV targets are processed using the same reagents and conditions. Furthermore, both target templates are amplified using the same reagents and reaction conditions. Because the ISC template and primers are present in the test samples, ISC product should be produced during amplification. If the ISC product is not formed, it is an indication that the test chemistry did not function correctly and the IHHNV test results are incorrect and should not be relied on. If the correct ISC product formation occurs, it indicates that the test chemistry worked correctly, and the IHHNV sample processing and test reactions are assumed to have functioned correctly so that the IHHNV test can be more accurately interpreted.

ISC primers can be selected from gene sequences of genes coding for structural proteins, metabolic enzymes or ribosomal products of the pathogen host species which are subject to IHHNV infections. For example, the ISC primers can be gene sequences derived from the shrimp actin gene, or 18S, 23S or 5S ribosomal genes of shrimp, or other constitutive genes. Suitable examples of ISC primer pairs include, but are not limited to, SEQ ID NOs:13, 14, and SEQ ID NOs:15,16, derived from the *Penaeus monodon* actin 1 gene (GenBank AF100986), as shown in Table 2.

TABLE 2

Internal Sample Control (ISC) Primer Sequences

| Primer, Direction | SEQ ID NO: | Actin 1 Gene Location (GenBank AF100986) |
|---|---|---|
| ActinF2, Forward | 13 | 391-411 |
| ActinR2, Reverse | 14 | 608-629 |
| ActinF3, Forward | 15 | 326-346 |
| ActinR3, Reverse | 16 | 553-574 |

In one embodiment, at least one pair of ISC primers is included in the nucleic acid amplification reagent mixture in order to produce an internal sample control product in the amplification reaction. In one embodiment, the at least one pair of ISC primers is selected from the group consisting of SEQ ID NOs:13,14, and SEQ ID NOs:15,16.

Additionally, an internal template control (ITC) can be used to advantage with the IHHNV test primers to aid in quantification of the test response. Primer requirements for the ITC are similar to those of the ISC primers with the exception that both the ITC template and primers are added to the amplification reagent mixture. The ITC primers are chosen so that they do not amplify genomic DNA or RNA from the test species, such as shrimp, which are subject to IHHNV. The ITC template is added at a known concentration so that the copy number per reaction is known. Because the ITC template is included in the amplification reagent mixture, the ITC product is produced during amplification. The amount of ITC product will vary from reaction to reaction depending on the amplification efficiency of the reaction and other variables. Since these same variables also affect the IHHNV DNA amplification, the amount of IHHNV product produced will be proportionately related to the amount of the ITC product produced in the reaction. Therefore, the copy number of the IHHNV template in the assay can be inferred from the proportionality between the ITC originally added, the ITC product formed, and the IHHNV product produced. Relative product formation can be determined in CT units when labeled internal probes are used or by the derivative of the melting curves at the products' respective melting temperature.

The ITC primer sequences can be rationally designed or derived from gene sequences from non-test species such as other viruses or genes from plants and animals which are not present in the test samples. In this way, sample materials do not contain other DNA or RNA which could be amplified by the ITC primers.

In one embodiment, at least one internal template control and at least one pair of ITC primers are included in the nucleic acid amplification reagent mixture in order to produce at least one ITC product in the amplification reaction.

A variety of detection methods, which are well known in the art, may be used in the methods disclosed herein. These detection methods include, but are not limited to, standard non-denaturing gel electrophoresis (e.g., acrylamide or agarose), denaturing gradient gel electrophoresis, temperature gradient gel electrophoresis, capillary electrophoresis, and fluorescence detection.

Fluorescence detection methods provide rapid and sensitive detection of amplification products. Fluorescence detection also provides the capability of real-time detection, wherein the formation of amplification products is monitored during the thermal cycling process. Additionally, the amount of the initial target may be quantified using fluorescence detection. Fluorescence detection may be done by adding a nucleic acid-binding fluorescent agent to the reaction mixture either before or after the thermal cycling process. Preferably, the nucleic acid-binding fluorescent agent is an intercalating dye that is capable of non-covalent insertion between stacked base pairs in the nucleic acid double helix. However, non-intercalating nucleic acid-binding fluorescent agents are also suitable. Non-limiting examples of nucleic acid-binding fluorescent agents useful in the methods of the invention are ethidium bromide and SYBR® Green I (available from Molecular Probes; Eugene, Oreg.). Addition of the nucleic acid-binding fluorescent agent to the reaction mixture prior to thermal cycling permits monitoring of the formation of amplification products in real-time, as described by Higuchi (U.S. Pat. No. 5,994,056). Thermal cyclers capable of real-time fluorescence measurements are commercially available from companies such as Applied Biosystems (Foster City, Calif.), MJ Research (Waltham, Mass.), and Stratagene (La Jolla, Calif.). Following amplification, confirmation of the amplification product can be assessed by determining the melting temperature of the product using methods know in the art, for example, by generating a melting curve using fluorescence measurement.

Fluorescence detection of amplification products may also be accomplished using other methods known in the art, such as the use of a fluorescently labeled probe. The probe comprises a complementary sequence to at least a portion of the amplification product. Non-limiting examples of such probes include TaqMan® probes (Applied Biosystems) and Molecular Beacons (Goel et al., *J. Appl. Microbiol.* 99(3):435-442 (2005)). For example, gene sequences for the construction of fluorescently labeled probes for use with the IHHNV primers disclosed herein can be selected by analysis of the IHHNV genes and test amplicons using commercially available analysis software such as Primer Express® v2.0 (Applied BioSystems Inc., Foster City Calif.), as described in detail in Example 11 below. Probe sequences are selected to fall within the proximal ends of the specific IHHNV test amplicons. Suitable probe sequences include, but are not limited, to the sequences set forth in SEQ ID NOs:17 and 18. The probes may be fluorescently labeled using methods known in the art, such as those described below for labeling hybridization probes. For real time fluorescent detection, probes can be dual labeled. For example, the 5' end of the probe can be labeled with a fluorophore, such as 6FAM™ (Applied BioSystems), and the 3' end can be labeled with a quencher dye, such as 6-carboxytetramethylrhodamine (TAMRA). In the case of a minor groove binding probe, the 3' end can be labeled with a quencher dye and a minor groove binder complex. Fluorescently labeled probes may be obtained from commercial sources such as Applied BioSystems.

In one embodiment, the invention provides a method for quantifying the amount of IHHNV in a sample. In this embodiment, DNA is provided from a sample suspected of containing IHHNV, as described above. The DNA is amplified with at least one pair of the oligonucleotide primers disclosed herein by thermal cycling between at least a denaturing temperature and an extension temperature in the presence of a nucleic acid-binding fluorescent agent or a fluorescently labeled probe. The amount of fluorescence generated by the nucleic acid-binding fluorescent agent or the fluorescently labeled probe is measured during thermal cycling. From the fluorescence measurements, a cycle threshold number is determined at which the amount of fluorescence generated by the nucleic acid-binding fluorescent agent or the fluorescently labeled probe reaches a fixed threshold value above a baseline value. The cycle threshold number is referred to herein as the CT number or value. The CT number can be determined manually or determined automatically by the instrument. To determine the CT number, the baseline fluorescence is determined for each sample during the initial amplification cycles. A mathematical algorithm is then employed to establish what a statistically significant change in fluorescence would need to be for the fluorescence signal to be above the background. The cycle number at which the florescence exceeds this threshold is referred to as the CT number. Typically, the more DNA present in the sample at the start of the thermal cycling, the fewer number of cycles it will take to reach the threshold value. Therefore, the CT number is inversely related to the initial amount of IHHNV in the sample. After the CT number for the IHHNV sample is determined, the amount of IHHNV originally present in the sample can be calculated by comparing the cycle threshold number determined for the IHHNV in the sample with a standard curve of the cycle threshold number versus the logarithm of template concentration determined using standard solutions of known concentration, as is well known in the art.

Nucleic Acid Hybridization Methods

The basic components of a nucleic acid hybridization test for IHHNV include a DNA probe, a sample suspected of containing IHHNV, and a specific hybridization method. Probes of the present invention are single stranded nucleic acid sequences which are complementary to the nucleic acid sequences to be detected and are "hybridizable" thereto. Typically in hybridization methods, the probe length can vary from as few as 5 bases to several kilobases and will depend upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

The DNA probes disclosed herein are derived from the IHHNV diagnostic primer sequences described above. As used herein the phrase "derived from the IHHNV diagnostic primer sequences" means that the DNA probes can be the IHHNV diagnostic primer sequences, the amplification product sequences obtained therefrom using a nucleic acid amplification method, portions of the IHHNV diagnostic primer sequences or the amplification product sequences, or the complete complementary sequences of any of the aforementioned sequences. The term "portion", as used above, refers to any part of the IHHNV diagnostic primer sequences or the amplification products obtained therefrom that is less than the complete sequence. Preferably, the length of the portion for use as a probe is at least about 15 bases, more preferably, at least about 20 bases. Non-limiting examples of DNA probes derived from the IHHNV diagnostic primer sequences include the IHHNV diagnostic primer sequences given as SEQ ID NOs: 1-8, the amplification product sequences given as SEQ ID NOs:9, 10, 11, and 12, and the complete complementary sequences of SEQ ID NOs:1-12.

The probe may be labeled to facilitate detection. Methods of attaching labels to nucleic acid probes are well known in the art. For example, the probe can be labeled during synthesis by incorporation of labeled nucleotides. Alternatively, probe labeling can be done by nick translation or end-labeling. The label may comprise a fluorophore for fluorescence detection, or a ligand, such as biotin, which is detected using an enzyme-labeled binding molecule that binds to the ligand (e.g., enzyme-labeled streptavidin) subsequent to hybridization.

In order to detect the presence of IHHNV in a sample suspected of containing IHHNV, such as shrimp or other crustaceans, DNA is provided from the sample, as described above. The sample DNA is made available to contact the probe before any hybridization of probe and target molecule can occur. Thus, the DNA must be free from the cell and placed under the proper conditions before hybridization can occur. Additionally in some embodiments, it may be desirable to purify the DNA to eliminate proteins, lipids, and other cell components. A variety of methods of nucleic acid purification, such as phenol-chloroform extraction, are known to those skilled in the art (Maniatis, supra). Additionally, kits are available from commercial sources for DNA extraction and purification (e.g., Isoquick® Nucleic Acid Extraction Kit (MicroProbe Corp., Bothell, Wash.); and QIAamp DNA Mini Kit (Qiagen, Valencia Calif.)). Pre-hybridization purification is particularly useful for standard filter hybridization assays.

In one embodiment, hybridization assays may be conducted directly on cell lysates, without the need to extract the nucleic acids. This eliminates several steps from the sample-handling process and speeds up the assay. To perform such assays on crude cell lysates, a chaotropic agent is typically added to the cell lysates prepared as described above. The chaotropic agent stabilizes nucleic acids by inhibiting nuclease activity. Furthermore, the chaotropic agent allows sensitive and stringent hybridization of short oligonucleotide probes to DNA at room temperature (Van Ness and Chen, Nucl. Acids Res. 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent is present at a final concentration of about 3 M. If desired, one can add formamide to the hybridization mixture, typically 30 to 50% by volume.

Hybridization methods are well defined and include solution (i.e., homogeneous) and solid phase (i.e., heterogeneous) hybridization methods. Typically, the sample DNA is probed (i.e. contacted under conditions which will permit nucleic acid hybridization) with a probe derived from the IHHNV diagnostic primer sequences disclosed herein. This involves contacting the probe and sample DNA in the presence of an inorganic or organic salt under the proper concentration and temperature conditions. The probe and sample nucleic acids must be in contact for a long enough time such that any possible hybridization between the probe and sample nucleic acid may occur. The concentration of probe or target in the mixture will determine the time necessary for hybridization to occur. The higher the probe or target concentration, the shorter the hybridization incubation time needed.

Various hybridization solutions can be employed. Typically, these may comprise from about 20 to 60% by volume, preferably 30%, of a polar organic solvent. A common hybridization solution employs about 30 to 50% by volume formamide, about 0.15 to 1 M sodium chloride, about 0.05 to 0.1 M buffers, such as sodium citrate, Tris-HCl, PIPES or HEPES (pH range about 6-9), about 0.05 to 0.2% detergent, such as sodium dodecylsulfate (SDS), between 0.5 to 20 mM EDTA, FICOLL (Amersham Bioscience Inc., Piscataway, N.J.) (molecular weight of about 300-500 kilodaltons), polyvinylpyrrolidone (molecular weight of about 250-500 kilodaltons), and serum albumin. Also included in a typical hybridization solution may be unlabeled carrier nucleic acids from about 0.1 to 5 mg/mL, fragmented nucleic DNA (e.g., calf thymus or salmon sperm DNA, or yeast RNA), and optionally from about 0.5 to 2% weight per volume glycine. Other additives may also be included, such as volume exclusion agents which include a variety of polar water-soluble or swellable agents (e.g., polyethylene glycol), anionic polymers (e.g., polyacrylate or polymethylacrylate), and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it, an immobilized nucleic acid capture probe that is unlabeled and is complementary to one portion of the sample DNA sequence. Probes particularly useful in the present invention are those derived from the present IHHNV diagnostic sequences, as described above. The captured DNA is detected using a second probe that is labeled, as described above, and is complementary to a different portion of the sample DNA sequence. The label may be detected using methods known in the art (e.g., fluorescence, chemiluminescence, binding pair enzyme assay and the like).

Hybridization methods may also be used in combination with nucleic acid amplification methods, such as PCR. For example, the instant IHHNV diagnostic sequences may be used as 3' blocked detection probes in either a homogeneous or heterogeneous assay format. For example, a probe generated from the instant sequences may be 3' blocked or non-participatory and will not be extended by, or participate in, a nucleic acid amplification reaction. Additionally, the probe incorporates a label that can serve as a reactive ligand that acts as a point of attachment for the immobilization of the probe/analyte hybrid or as a reporter to produce detectable signal. Accordingly, genomic DNA isolated from a sample suspected of harboring the IHHNV is amplified by standard primer-directed amplification protocols in the presence of an excess of the 3' blocked detection probe to produce amplification products. Because the probe is 3' blocked, it does not participate or interfere with the amplification of the target. After the final amplification cycle, the detection probe anneals to the relevant portion of the amplified DNA and the annealed complex is then captured on a support through the reactive ligand.

The instant probe is versatile and may be designed in several alternate forms. The 3' end of the probe may be blocked from participating in a primer extension reaction by the attachment of a replication inhibiting moiety. Typical replication inhibitor moieties include, but are not limited to, dideoxynucleotides, 3' deoxynucleotides, a sequence of mismatched nucleosides or nucleotides, 3' phosphate groups and chemical agents, such as biotin, dinitrophenol, fluorescein, rhodamine, and carbon chains. The replication inhibitor is covalently attached to the 3' hydroxy group of the 3' terminal nucleotide of the non-participatory probe during chemical synthesis, using standard cyanoethyl phosphoramidite chemistry. This process uses solid phase synthesis chemistry in which the 3' end is covalently attached to an insoluble support (controlled pore glass, or "CPG") while the newly synthesized chain grows on the 5' terminus. Within the context of the present invention, 3-deoxyribonucleotides are the preferred replication inhibitors. Cordycepin (3-deoxyadenosine) is most preferred. Since the cordycepin will be attached to the 3' terminal end of the probe, the synthesis is initiated from a cordycepin covalently attached to CPG, 5-dimethoxytrityl-N-benzoyl-3-deoxyadenosine (cordycepin), 2-succinoyl-long chain alkylamino-CPG (Glen Research, Sterling, Va.). The dimethoxytrityl group is removed and the initiation of the chain synthesis starts at the deprotected 5' hydroxyl group of the solid phase cordycepin. After the synthesis is complete, the oligonucleotide probe is cleaved off the solid support leaving a free 2' hydroxyl group on the 3'-terminally attached cordycepin. Other reagents can also be attached to the 3' terminus during the synthesis of the non-participatory probe to serve as replication inhibitors. These include, but are not limited to, other 3-deoxyribonucleotides, biotin, dinitrophenol, fluorescein, and digoxigenin. CPG supports, derivatized with each of these reagents, are available from commercial sources (e.g., Glen Research, Sterling, Va.; and CLONTECH Laboratories, Palo Alto, Calif.).

Alternatively, asymmetric amplification may be used to generate a strand complementary to the detection probe. Asymmetric PCR conditions for producing single-stranded DNA are similar to the conditions described above for PCR; however, the primer concentrations are adjusted so that one primer is in excess and the other primer is limiting. It is contemplated that this procedure would increase the sensitivity of the method. This improvement in sensitivity would occur by increasing the number of available single strands for binding with the detection probe.

Assessment of Infection Risk and DNA Damage or IHHNV Inactivation

The methods for detecting the presence of and quantifying the amount of IHHNV in a sample disclosed herein may be used to assess the extent of DNA damage or IHHNV inactivation. For example, the methods disclosed herein may be used in combination with a chemical treatment to improve the health and grow out of shrimp. Specifically, during production and grow-out, the shrimp, samples taken from the production facilities, or samples taken from the shrimp's environment may be sampled and tested for the presence of IHHNV using the methods disclosed herein. If IHHNV is found, the facilities and/or the shrimp can be treated to kill or control the virus. Because of the high sensitivity of the test, IHHNV can be detected early, before devastation and loss of the crop. Thus, use of the methods disclosed herein in combination with chemical intervention can improve production efficiency and yield. Examples of chemical treatments include, but are not limited to, oxidative disinfectants such as Virkon® S disinfectant (a registered trademark of E.I. Du Pont de Nemours and Co.), peracetic acids, hydrogen peroxide, permanganate, potassium monopersulfate, hypochlorous acid, hypochlorite, iodine and the like; probiotics, immunostimulants, feed supplements, and recombinant protein/nucleic acids that prevent viral host binding. After the chemical treatment, the shrimp or the production environment can be sampled and retested to determine if the treatment was successful in eradicating the virus.

In another embodiment, it is anticipated that the primers disclosed herein may be used in various combinations to ascertain the integrity and extent of damage to the viral genome resulting from chemical treatment. For example, the forward primer of IHHNV1F (SEQ ID NO:1) and the reverse primer of IHHNV2R (SEQ ID NO:4) may be used in combination to produce an amplification product of 480 bases. This longer product can form only if the viral genome remains intact and undamaged. Therefore, by comparing the ratio of the smaller products (SEQ ID NO:9 or SEQ ID NO:10) to the longer product formed during amplification (or the absence of the longer product), the extent of viral genome damage resulting from chemical treatment or intervention can be assessed. This can aid in establishing the efficacy of chemical treatment or intervention. In like manner, SEQ ID NO:1 or SEQ ID NO:8 may be used in combination with other primers disclosed herein to interrogate the integrity of longer segments of the IHHNV genome.

Detection Kits

In another embodiment, the invention provides a kit for the detection of IHHNV based on a nucleic acid amplification method. The kit comprises at least one pair of IHHNV diagnostic primer sequences, as described above. Additionally, the kit may further comprise at least one of the following reagents: a thermostable DNA polymerase, a mixture of four different deoxynucleotide triphosphates, a nucleic acid-binding fluorescence agent, at least one pair of internal sample control primers, at least one internal template control and at least one pair of internal template control primers, and a probe comprising a complementary sequence to a portion of at least one region of nucleic acid within the IHHNV genome which is capable of being amplified with the IHHNV diagnostic primer sequences contained in the kit. The primers and other reagents of the kit may be in various forms, such as a liquid, dried, or tablet and may be present in any suitable container or multiple containers, such as vials, tubes, and the like.

In another embodiment, the invention provides a kit for the detection of IHHNV based on a sandwich assay hybridization method. This kit comprises a first component for the collection of samples from a shrimp or other crustacean suspected of having contracted the IHHNV and buffers for the disbursement and lysis of the sample. A second component includes media in either dry or liquid form for the hybridization of target and probe nucleic acids, as well as for the removal of undesirable and non-hybridized forms by washing. A third component includes a solid support (e.g., dipstick, bead, and the like) upon which is fixed (or to which is conjugated) unlabeled nucleic acid probe(s) that is (are) derived from the isolated IHHNV diagnostic primer sequences disclosed herein. A fourth component contains labeled probe that is complementary to a second and different region of the same DNA strand to which the immobilized, unlabeled nucleic acid probe of the third component is hybridized. The labeled probe may also be derived from the isolated IHHNV diagnostic primer sequences disclosed herein.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "sec" means second(s), "min" means minute(s), "hr" means hour(s), "d" means day(s), "µL" means microliter(s), "mL" means milliliter(s), "L" means liter(s), "µM" means micromolar, "mM" means millimolar, "nM" means nanomolar, "M" means molar, "mmol" means millimole(s), "µmol" mean micromole(s), "ng" means nanogram(s), "fg" means femtogram(s), "µg" means microgram(s), "mg" means milligram(s), "g" means gram(s), "nm" means nanometer(s), "mU" means milliunit(s), "U" means unit(s), "rxn" means reaction(s), "PCR" means polymerase chain reaction, "OD" means optical density, "$OD_{260}$" means the optical density measured at a wavelength of 260 nm, "$OD_{280}$" means the optical density measured at a wavelength of 280 nm, "$OD_{280/260}$" means the ratio of the $OD_{280}$ value to the $OD_{260}$ value, "rpm" means revolutions per minute, "CT" means the cycle number at which the buildup in fluorescence in the reaction exceeds the detection threshold, and "SPF" means certified specific pathogen free.

General Methods

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory Press, Cold Spring Harbor, N.Y., 1984, and by Ausubel, F. M. et al., *Current Protocols in Molecular Biology*, Greene Publishing Assoc. and Wiley-Interscience, N.Y., 1987.

Analysis of genome sequences and primer designates was accomplished using the Vector NTI® Software Suite available from InforMax Inc. (Bethesda, Md.).

Enzymes and reagents used herein were purchased from the following vendors:
Applied Biosystems, Foster City, Calif.: AmpliTaq (Catalog No. N808-0160);
New England Biolabs, Beverly, Mass.: deoxynucleotide solution mix (Catalog No. N0447S);
Sigma Genosys, The Woodlands, Tex.: Oligonucleotides;
Invitrogen Life Technologies, Carlsbad, Calif.: 4% Agarose E-gels (Catalog No. G6018-02);
Qiagen, Valencia, Calif.: Proteinase K (Catalog No. 19131); and
RNase A, DNase-free (Catalog No. 19101).

Additionally, kits and reagents were purchased from the following vendors: SYBR® Green PCR Master Mix (Applied Biosystems, Foster City, Calif.; Catalog No. 4309155); and QIAamp DNA Mini Kit (Qiagen, Valencia, Calif.; Catalog No. 51304).

All shrimp DNA samples were obtained from Donald V. Lightner, Department of Veterinary Science and Microbiology, The University of Arizona, Tucson, Ariz. 85721, USA. These included DNA samples from certified disease free shrimp (SPF) and infected shrimp containing *Penaeus monodon*-type baculoviruses (MBV), Taura syndrome virus (TSV), white spot syndrome virus (WSSV), yellow head virus of *P. monodon* (YHV), Infectious Hypodermal and Hematopoietic Necrosis virus (IHHNV) and Infectious Myonecrosis virus (IMNV).

Templates and Primers

DNA oligonucleotide sequences for synthesis of the synthetic IHHNV templates were prepared from the Infectious Hypodermal and Hematopoietic Necrosis Virus (IHHNV) DNA genome (GenBank Accession Number AF218266; Bonami, J. R. et al., *J. Gen. Virology* 71 (Pt 11):657-2664 (1990)) and were synthesized using standard phosphoramidite chemistry or purchased commercially (Sigma Genosys Company, The Woodlands, Tex.). The DNA concentration and copy number of the synthetic template targets and samples were measured spectrophotometrically at 260 nm ($OD_{260}$). The templates were diluted to specific copy numbers in purified water and were used as the positive controls and standards for assay quantification. Table 3 displays the genome locations, sequence identification, and lengths of the template targets. The sequences of the primers useful for IHHNV detection are given as SEQ ID NOs:1-8.

TABLE 3

Template Sequences

| Template | Size (bp) | SEQ ID NO: | IHHNV Genome Location (GenBank AF218266) |
|---|---|---|---|
| IHHNV 1T | 119 | 9 | 682-800 |
| IHHNV 2T | 100 | 10 | 1062-1161 |
| IHHNV 3T | 108 | 11 | 1749-1856 |
| IHHNV 4T | 116 | 12 | 3417-3532 |

Examples 1-4

Demonstration of IHHNV Assay Using Synthetic Targets

The purpose of these Examples was to demonstrate the detection of the IHHNV synthetic templates using PCR amplification with the primers disclosed herein.

Template standards were prepared by 10 fold serial dilutions of the synthetic IHHNV templates (described above) in DNase free water. Generally, template concentrations of the standards ranged from $10^7$ to 0 copies/µL. A master mix was prepared by adding 25 µL of the SYBR® Green PCR Master Mix (Applied Biosystems, Foster City, Calif.; Catalog No. 4309155) with 125 nM each of the appropriate IHHNV forward and reverse primers, as shown in Table 4, and enough DNase free water to make up a final volume of 45 µL/reaction. The master mix was maintained on ice until use.

For each reaction, 5 µL of a template standard was first added to the PCR reaction well and then 45 µL of the master mix was added. The reactions were then thermal cycled for 40 cycles using a temperature program of 95° C. for 15 sec and 60° C. for 1 min with an initial denaturing step of 95° C. for 10 min. The amplifications were carried out in a MicroAmp optical 96-well reaction plate using the ABI PRISM 7900 thermal cycler (Applied Biosystems, Foster City, Calif.). During each cycle, PCR product formation was detected by monitoring the increase in fluorescence arising from the interaction of the SYBR® Green reporter dye with the DNA amplification products. After completion of PCR, a dissociation curve (melting curve) was generated over the range of 60° C. to 95° C. Data were analyzed using the ABI PRISM 7900 SDS software. In addition, PCR product formation was analyzed by agarose gel electrophoresis using 4% agarose Egels (Invitrogen Life Technologies, Carlsbad, Calif.; Cat No. G6018-02) and the gel manufacture's protocols.

The results, summarized in Table 4, demonstrate that the appropriate size amplicon product was produced for each primer set when the appropriate IHHNV template was present. The minimum detectable template level was between 2 and 100 copies/rxn, depending on the primers used. Samples containing no template produced no detectable product.

Amplification (CT) and amplicon product formation were, respectively, inversely and directly proportional to the logarithm of the starting template concentration.

TABLE 4

Results of PCR Amplification using a Synthetic Target

| Example | Forward Primer, SEQ ID NO: | Reverse Primer, SEQ ID NO: | Template SEQ ID NO: | Product Size (bp) | Minimum Detectable Template (copies/rxn) |
|---|---|---|---|---|---|
| 1 | 1 | 2 | 9 | 119 | 2 to 10 |
| 2 | 3 | 4 | 10 | 100 | 2 to 10 |
| 3 | 5 | 6 | 11 | 108 | 2 to 10 |
| 4 | 7 | 8 | 12 | 116 | 100 to 500 |

Examples 5-8

Detection and Quantification of IHHNV DNA from Infected Shrimp Tissue

The purpose of these Examples was to demonstrate the detection and quantification of IHHNV in infected shrimp using a PCR assay with the primers disclosed herein.

In these Examples, serial dilutions of the appropriate synthetic template IHHNV DNA (described above) ranging from $10^6$ to $10^0$ copies per reaction were amplified using the conditions stated in Examples 1-4. A standard curve (not shown) was generated using the CT values determined from each of the synthetic template concentrations by plotting the CT values, with 95% confidence intervals, against the logarithm of the initial template copy numbers in the standards. The slope of this curve (i.e., CT versus log concentration) was then used to estimate the copies of viral genome in an unknown sample from their respective CT values.

Genomic DNA from shrimp infected with a Hawaii strain of the IHHNV was used. The total DNA (347 ng/µL) was serially diluted in purified water and used to provide a series of samples ranging in DNA concentration from 1 ng/µL to 1 fg/µL of total DNA. Negative controls included a water control containing no template and two DNA shrimp samples (50 ng/rxn) from two strains of non-infected (SPF) shrimp (*Litopenaeus vannamei* and *Penaeus monodon*).

The diluted samples were then amplified using one of the primer pairs (see Table 5) and the same amplification, master mix, thermal cycling conditions and instrument stated in Examples 1-4. The CT value for each diluted DNA sample was then assessed from the PCR amplification reactions. The copies of viral genome in the samples were then estimated from the CT value and the slope of the standard CT versus log template concentration plot. The PCR products were also analyzed by agarose gel electrophoresis, as described in Examples 1-4.

The results are summarized in Table 5. In the table, the IHHNV copy number per reaction is given as the mean of three replicates along with the 95% confidence interval. The results indicate that all of the primer sets produced the correct amplicon product size from the infected shrimp DNA and detected IHHNV DNA in the infected shrimp samples. The detection limits ranged from about 2 copies/rxn to about 40 copies/rxn of the viral genome, depending on the primer pair used. No amplification products were detected in the water control sample or the two SPF shrimp samples. The results obtained with the negative control samples demonstrate that the assay is non-responsive to non-viral DNA from the two shrimp strains tested.

TABLE 5

Results of Detection of DNA from IHHNV Infected Shrimp

| Example | Forward primer SEQ ID NO: | Reverse primer SEQ ID NO: | Infected Shrimp DNA/rxn (ng) | CT | IHHNV copies/rxn |
|---|---|---|---|---|---|
| 5 | 7 | 8 | 1 | 18.9 | $46 \pm 2 \times 10^4$ |
| 5 | 7 | 8 | 0.1 | 21.2 | $3.9 \pm 0.2 \times 10^4$ |
| 5 | 7 | 8 | 0.01 | 25.1 | $1.0 \pm 0.1 \times 10^3$ |
| 5 | 7 | 8 | 0.001 | 30.4 | $51 \pm 0.5 \times 10^2$ |
| 5 | 7 | 8 | 0.0001 | 34.9 | $4 \pm 0.2 \times 10^1$ |
| 5 | 7 | 8 | 0.00001 | >40 | 0 |
| 5 | 7 | 8 | 0.000001 | >40 | 0 |
| 5 | 7 | 8 | 0 (water) | >40 | 0 |
| 5 | 7 | 8 | 0 (SPF *L. vannamei* (50 ng)) | >40 | 0 |
| 5 | 7 | 8 | 0 (SPF *P. monodon* (50 ng)) | >40 | 0 |
| 6 | 1 | 2 | 1 | 25.3 | $1324 \pm 83$ |
| 6 | 1 | 2 | 0.1 | 28.7 | $138 \pm 4$ |
| 6 | 1 | 2 | 0.01 | 32.2 | $13 \pm 2$ |
| 6 | 1 | 2 | 0.001 | 35.7 | $2 \pm 1$ |
| 6 | 1 | 2 | 0.0001 | >40 | 0 |
| 6 | 1 | 2 | 0.00001 | >40 | 0 |
| 6 | 1 | 2 | 0.000001 | >40 | 0 |
| 6 | 1 | 2 | 0 (water) | >40 | 0 |
| 6 | 1 | 2 | 0 (SPF *L. vannamei* (50 ng)) | >38 | 0 |
| 6 | 1 | 2 | 0 (SPF *P. monodon* (50 ng)) | >38 | 0 |
| 7 | 3 | 4 | 1 | 24.8 | $868 \pm 21$ |
| 7 | 3 | 4 | 0.1 | 27.9 | $113 \pm 12$ |
| 7 | 3 | 4 | 0.01 | 31.9 | $9 \pm 2$ |
| 7 | 3 | 4 | 0.001 | 35.2 | $1 \pm 1$ |
| 7 | 3 | 4 | 0.0001 | >40 | 0 |
| 7 | 3 | 4 | 0.00001 | >40 | 0 |
| 7 | 3 | 4 | 0.000001 | >40 | 0 |
| 7 | 3 | 4 | 0 (water) | >40 | 0 |
| 7 | 3 | 4 | 0 (SPF *L. vannamei* (50 ng)) | >40 | 0 |
| 7 | 3 | 4 | 0 (SPF *P. monodon* (50 ng)) | >40 | 0 |

TABLE 5-continued

Results of Detection of DNA from IHHNV Infected Shrimp

| Example | Forward primer SEQ ID NO: | Reverse primer SEQ ID NO: | Infected Shrimp DNA/rxn (ng) | CT | IHHNV copies/rxn |
|---|---|---|---|---|---|
| 8 | 5 | 6 | 1 | 26.6 | 4800 ± 280 |
| 8 | 5 | 6 | 0.1 | 30.0 | 433 ± 3 |
| 8 | 5 | 6 | 0.01 | 33.7 | 35 ± 4 |
| 8 | 5 | 6 | 0.001 | 36.7 | 5 ± 1 |
| 8 | 5 | 6 | 0.0001 | >40 | 0 |
| 8 | 5 | 6 | 0.00001 | >40 | 0 |
| 8 | 5 | 6 | 0.000001 | >40 | 0 |
| 8 | 5 | 6 | 0 (water) | >40 | 0 |
| 8 | 5 | 6 | 0 (SPF *L. vannamei* (50 ng)) | >38 | 0 |
| 8 | 5 | 6 | 0 (SPF *P. monodon* (50 ng)) | >38 | 0 |

Example 9

The purpose of this Example was to demonstrate that the primers disclosed herein amplify DNA from IHHNV strains from different geographical areas of the World, but do not amplify DNA or RNA of shrimp infected with other shrimp pathogens.

In this Example, DNA from shrimp infected with other shrimp pathogens was used. Specifically, DNA samples isolated from shrimp infected with IHHNV strains from different geographical regions (Hawaii, Philippines, Thailand, Panama, Mexico Mozambique and Madagascar) along with non-IHHNV shrimp viruses (MBV, WSSV, YHV and IMNV) were tested using the primers and PCR method described in Examples 5-8.

All IHHNV strains were detected with similar detection limits as the strain described in Examples 5-8. No PCR amplification was observed when testing the non-IHHNV infected shrimp DNA samples. These findings taken together demonstrate that the IHHNV PCR primers and methods disclosed herein are selective for IHHNV and that the primers do not react with shrimp DNA or other shrimp viruses.

Example 10

Detection of IHHNV DNA in Combination with an Internal Sample Control Using PCR

The purpose of this Example was to demonstrate that the IHHNV primers disclosed herein can be used in combination with internal sample control (ISC) primers to produce an ISC product in addition to the IHHNV product. The results presented below demonstrate that the ISC primers independently amplify sample DNA and do not interfere with the amplification of IHHNV DNA. The presence of the ISC product provides a marker that can be used as an indication that sample DNA of sufficient quantity and quality had been recovered for testing.

ISC primers were derived from the *Penaeus monodon* actin 1 gene sequence (GenBank: AF100986). In order to promote preferential amplification of the IHHNV amplicon, the ISC primers were designed to amplify a DNA fragment that was larger than the target IHHNV amplicons. The ISC primer pair sequences are given as SEQ ID NOs:13,14, and SEQ ID NOs:15,16 (see Table 2).

Samples containing IHHNV and shrimp actin DNA were prepared by 10-fold serial dilutions of a genomic DNA preparation from a IHHNV infected shrimp (*Penaeus monodon*) with DNase free water. The DNA content of the samples ranged from 0.1 ng to 0.1 pg per reaction. Genomic shrimp DNA (10 ng) from a non-infected shrimp was then added to each IHHNV sample and to negative control samples containing no IHHNV DNA.

A master PCR mix was prepared by combining 15 µL/reaction of the SYBR® Green PCR Master Mix (Applied Biosystems, Foster City, Calif.; Catalog No. 4309155) with a volume of primer stock solutions (20 µM for each of the IHHNV primers and 10 µM for each of the actin primers) sufficient to give a final concentration of 125 nM for each of the IHHNV4 forward and reverse primers (SEQ ID NOs:7 and 8, respectively) and 32 nM for each of the actin2 forward and reverse primers (SEQ ID NOs:13 and 14). DNase free water was added to make up a final volume of 25 µL/reaction. The master mix was maintained on ice until use.

For each reaction, 5 µL of the samples was first added to the PCR reaction wells and then 25 µL of the master mix was added. The reactions were then thermal cycled for 40 cycles using a temperature program of 95° C. for 15 sec and 60° C. for 1 min with an initial denaturing step of 95° C. for 5 min. Amplification was carried out in a MicroAmp optical 96-well reaction plate using the ABI PRISM 7900 thermal cycler (Applied Biosystems, Foster City, Calif.).

During each cycle, product formation was monitored by the CT value determined from the increase in fluorescence arising from the interaction of the SYBR® Green reporter dye with the DNA amplification products, as described above. After 40 cycles a dissociation curve (melting curve) was generated over the range of 60° C. to 95° C. Data were analyzed using the ABI PRISM 7900 SDS software. In addition, PCR product formation was analyzed by agarose gel electrophoresis using 4% agarose Egels (Invitrogen Life Technologies, Carlsbad, Calif.; Cat No. G6018-02) and the gel manufacture's protocols.

The results obtained using ISC primers ActinF2 (SEQ ID NO:13) and ActinR2 (SEQ ID NO:14) are shown in FIGS. 1A and 1B, which demonstrate the simultaneous amplification of both template targets. The specific IHHNV DNA produced a 116 bp product with a melting temperature of 80° C. The actin ISC produced a 239 bp product (Tm=83.8° C.). The IHHNV product and actin internal control products were detected by both melting curve analysis (FIG. 1A) and gel electrophoresis (FIG. 1B) based on these size and melting temperature differences. In the absence of IHHNV target and at various IHHNV target concentrations, formation of the ISC product was detected as a single melting-temperature peak at 83.8° C. (as shown in FIG. 1A) and by electrophoresis (as shown in FIG. 1B). In all samples containing the IHHNV template, the specific IHHNV amplicon was detected by both melting temperature (Tm=80° C.) and by gel electrophoresis. These results demonstrate that the actin ISC template co-amplifies with the IHHNV template and that the PCR amplification and limit of detection of the PCR assay (0.1 pg IHHNV DNA) are unaffected by the presence of the ISC.

Example 11

Real Time Detection of IHHNV DNA Using a Fluorescently Labeled Probe

This Example demonstrates that the IHHNV primers disclosed herein can be used in combination with a fluorescently labeled probe for real time detection and quantification of IHHNV.

Gene sequences for construction of the fluorescently labeled probes were selected by analysis of the IHHNV genes and test amplicons using Primer Express® v2.0 software, purchased from Applied BioSystems Inc. (Foster City, Calif. 94404). The probe sequences were chosen to fall within the proximal ends of the specific IHHNV test amplicons and were 50 to 110 bases in length, depending on the size and sequence of the amplicon. Preference for the probe sequences was given to regions with G/C content of 30 to 80% and with higher C than G content, and with no 5' G. Generally, probe sequences were selected having a Tm of 8 to 10° C. above the respective Tm of the test primers. Probes sequences which cross-hybridized to other species were not selected for use. The probe sequences selected to meet these criteria are listed in Table 6.

For real-time detection, the probe sequences were dual labeled. Two different labeling approaches were employed. The 5' end of the probes were labeled with a fluorophore (6FAM™, Applied Biosystems). The 3' end was labeled either with a quencher dye or in the case of minor grove binding (MGB) probe, the 3' end was labeled with a quencher dye and a minor grove binder complex. The labeled probes were prepared and purchased commercially from Applied BioSystems. The data presented below was obtained using the IHHNV4PT probe (SEQ ID NO:18). It is anticipated that the IHHNV4PM probe (SEQ ID NO:17) may be used in a similar manner.

Template standards were prepared by 10-fold serial dilutions of the synthetic IHHNV templates (described above) in DNase free water. Generally, template concentrations of the standards ranged from $10^7$ to 0 copies/µL. A master mix was prepared by combining 25 µL/reaction of the TaqMan® Universal Master Mix (Applied Biosystems, Foster City, Calif.; Catalog No. 4326708) with a volume of primer stock solutions (20 µM for each of the IHHNV primers) sufficient to give a final concentration of 125 nM for each of the IHHNV forward and reverse primers, as shown in Table 7, a volume of the probe stock solution to give a final concentration of 50 nM and enough DNase free water to make up a final volume of 45 µL/reaction. The master mix was maintained on ice until use.

For each reaction, 5 µL of template standard and then 45 µL of the master mix were added to each PCR reaction well. The reactions were then thermal cycled for 40 cycles using a temperature program of 95° C. for 15 sec and 60° C. for 1 min with an initial denaturing step of 95° C. for 10 min. The amplifications were carried out in a MicroAmp optical 96-well reaction plate using the ABI PRISM 7900 thermal cycler (Applied Biosystems, Foster City, Calif.). During each cycle, PCR product formation was detected by monitoring the increase in fluorescence arising from the fluorescently labeled probe.

Data were analyzed using ABI SDS 2.2 software. In addition, PCR product formation was analyzed by agarose gel electrophoresis using 4% agarose Egels (Invitrogen Life Technologies, Carlsbad, Calif.; Cat No. G6018-02) and the manufacture's protocols.

The results, summarized in Table 7, demonstrate that the appropriate size amplicon product was produced when the appropriate IHHNV template was present. The minimum detectable template level was 50 copies/rxn. Samples containing no template produced no detectable product.

Amplification (CT) and amplicon product formation were, respectively, inversely and directly proportional to the logarithm of the starting template concentration.

TABLE 6

Fluorescent Labeled Probe Sequences

| Probe | SEQ ID NO: | GenBank No: | 5' Location | Label | 3' Label(s) |
|---|---|---|---|---|---|
| IHHNV4PM | 17 | AF218266 | 3444-3459 | FAM[1] | MGB[2] |
| IHHNV4PT | 18 | AF218266 | 3481-3505 | FAM | TAMRA[3] |

[1]FAM is 6FAM ™ reagent, Applied Biosystems
[2]MGB is MGB ™ Applied Biosystems
[3]TAMRA is 6-carboxytetramethylrhodamine

TABLE 7

Results of PCR Amplification Using a Synthetic Target

| Forward Primer, SEQ ID NO: | Reverse Primer, SEQ ID NO: | Template SEQ ID NO: | Probe SEQ ID NO: | Product Size (bp) | Minimum Detectable Template (copies/rxn) |
|---|---|---|---|---|---|
| 7 | 8 | 12 | 18 | 116 | 50 |

What is claimed is:

1. An isolated IHHNV diagnostic primer sequence as set forth in SEQ ID NO: 1 or an isolated nucleic acid molecule that is completely complementary to SEQ ID NO:1, wherein the primer sequence corresponds to a portion of the IHHNV genome which is diagnostic for the presence of IHHNV.

2. An isolated IHHNV diagnostic primer sequence as set forth in SEQ ID NO:2 or an isolated nucleic acid molecule that is completely complementary to SEQ ID NO:2, wherein the primer sequence corresponds to a portion of the IHHNV genome which is diagnostic for the presence of IHHNV.

3. An isolated IHHNV diagnostic primer sequence as set forth in SEQ ID NO:3 or an isolated nucleic acid molecule that is completely complementary to SEQ ID NO:3, wherein the primer sequence corresponds to a portion of the IHHNV genome which is diagnostic for the presence of IHHNV.

4. An isolated IHHNV diagnostic primer sequence as set forth in SEQ ID NO:4 or an isolated nucleic acid molecule that is completely complementary to SEQ ID NO:4, wherein the primer sequence corresponds to a portion of the IHHNV genome which is diagnostic for the presence of IHHNV.

5. An isolated IHHNV diagnostic primer sequence as set forth in SEQ ID NO:5 or an isolated nucleic acid molecule that is completely complementary to SEQ ID NO:5, wherein the primer sequence corresponds to a portion of the IHHNV genome which is diagnostic for the presence of IHHNV.

6. An isolated IHHNV diagnostic primer sequence as set forth in SEQ ID NO:6 or an isolated nucleic acid molecule that is completely complementary to SEQ ID NO:6, wherein the primer sequence corresponds to a portion of the IHHNV genome which is diagnostic for the presence of IHHNV.

7. An isolated IHHNV diagnostic primer sequence as set forth in SEQ ID NO:7 or an isolated nucleic acid molecule that is completely complementary to SEQ ID NO:7, wherein the primer sequence corresponds to a portion of the IHHNV genome which is diagnostic for the presence of IHHNV.

8. An isolated IHHNV diagnostic primer sequence as set forth in SEQ ID NO:8 or an isolated nucleic acid molecule that is completely complementary to SEQ ID NO:8, wherein the primer sequence corresponds to a portion of the IHHNV genome which is diagnostic for the presence of IHHNV.

9. A pair of two different IHHNV diagnostic primer sequences of any of SEQ ID NOs:1-8 wherein the pair is capable of priming a nucleic acid amplification reaction that amplifies a region of nucleic acid within the IHHNV genome which is diagnostic for the presence of IHHNV.

10. A pair of two different IHHNV diagnostic primer sequences according to claim 9 wherein the pair is selected from the group consisting of SEQ ID NOs: 1 and 2, SEQ ID NOs:3 and 4, SEQ ID NOs:5 and 6, SEQ ID NOs:7 and 8, and SEQ ID NOs:1 and 4.

11. A kit for the detection of IHHNV comprising at least one pair of IHHNV diagnostic primer sequences of claim 9, wherein said kit is diagnostic for the presence of IHHNV.

12. A kit for the detection of IHHNV according to claim 10 wherein the kit further comprises at least one reagent selected from the group consisting of a thermostable polymerase, a mixture of four different deoxynucleotide triphosphates, a nucleic acid-binding fluorescent molecule, at least one pair of internal sample control primers, at least one internal template control and at least one pair of internal template control primers, and a probe comprising a complementary sequence to a portion of at least one region of nucleic acid within the IHHNV genome which is capable of being amplified with the at least one pair of IHHNV diagnostic primer sequences.

13. A method for detecting the presence of IHHNV in a sample comprising:
(i) providing DNA from a sample suspected of containing the IHHNV; and
(ii) probing the DNA with a probe derived from the isolated IHHNV diagnostic primer sequence of any of claims 1-8 under suitable hybridization conditions;
wherein the identification of a hybridizable nucleic acid fragment confirms the presence of IHHNV.

14. A method for detecting the presence of IHHNV in a sample according to claim 13 wherein the probe derived from the isolated IHHNV diagnostic primer sequence is selected from the group consisting of SEQ ID NOs:1, 2, 3, 4, 5, 6, 7 8, 9, 10, 11, 12, and the complete complimentary sequences thereof.

15. A method according to claim 13 wherein the probe contains a replication inhibiting moiety at the 3' end.

16. A method according to claim 15 wherein the replication inhibiting moiety is selected from the group consisting of dideoxynucleotides, 3' deoxynucleotides, a sequence of mismatched nucleosides or nucleotides, 3' phosphate groups and chemical agents.

17. A method according to claim 16 where in the 3' deoxynucleotide is cordycepin.

18. A method for detecting the presence of IHHNV in a sample comprising:
(i) providing DNA from a sample suspected of containing IHHNV; and
(ii) amplifying the DNA with at least one pair of IHHNV diagnostic primer sequences of claim 9 such that amplification products are generated;
wherein the presence of amplification products confirms the presence of IHHNV.

19. A method for detecting the presence of IHHNV in a sample according to claim 18 wherein the amplifying of (ii) is done using the polymerase chain reaction.

20. A method for detecting the presence of IHHNV in a sample according to claim 18 wherein the amplifying of (ii) is done in the presence of a nucleic acid-binding fluorescent agent or a fluorescently labeled probe and the presence of amplification products is confirmed using fluorescence detection.

21. A method according to claim 20 wherein the fluorescently labeled probe is selected from the group consisting of SEQ ID NO:17 and SEQ ID NO:18.

22. A method according to claim 18 wherein at least one pair of internal sample control primers is included in the amplifying of (ii) to produce an internal sample control product.

23. A method according to claim 22 wherein the at least one pair of internal sample control primers is selected from the group consisting of SEQ ID NOs:13,14 and SEQ ID NOs:15, 16.

24. A method according to claim 18 wherein at least one pair of internal template control primers and at least one internal template control are included in the amplifying of (ii) to produce an internal template control product.

25. A method for quantifying the amount of IHHNV in a sample comprising:
(i) providing DNA from a sample suspected of containing IHHNV;
(ii) amplifying the DNA with at least one pair of IHHNV diagnostic primer sequences of claim 9 by thermal cycling between at least a denaturing temperature and an extension temperature in the presence of a nucleic acid-binding fluorescent agent or a fluorescently labeled probe;

(iii) measuring the amount of fluorescence generated by the nucleic acid-binding fluorescent agent or the fluorescently labeled probe during the thermal cycling;

(iv) determining a cycle threshold number at which the amount of fluorescence generated by the nucleic acid-binding fluorescent agent or the fluorescently labeled probe reaches a fixed threshold value above a baseline value; and (v) calculating the amount of IHHNV in the sample by comparing the cycle threshold number determined for the IHHNV in the sample with a standard curve of the cycle threshold number versus the logarithm of template concentration determined using standard solutions of known concentration.

26. A method according to claim 25 where in the fluorescently labeled probe is selected from the group consisting of SEQ ID NO:17 and SEQ ID NO:18.

27. A method according to any of claims 13, 18, or 25 wherein the method further comprises the steps of:

a) treating an environment from which the sample was obtained with a chemical treatment to kill or control the IHHNV; and b) repeating the steps of the method of claims 13, 18, or 25 on another sample taken from the environment in order to assess IHHNV inactivation by the chemical treatment.

28. A method according to any of claims 13, 18, or 25 wherein the method further comprises the step of: treating an environment from which the sample was obtained with a chemical treatment to kill or control the IHHNV in order to improve the health and grow-out of shrimp.

* * * * *

SEQUENCE LISTING

<160> NUMBER OF SEQ ID NOS: 18

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
cattctaccg tggtgcttca tagg

```
<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ttcgtcgtcg ggatgacagt gt                                              22

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
gatcctaagg tctgcgtgga taacc                                           25

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
caacacttcc aagggaggtt tctga                                           25

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
agatacggta ttgaacggct ttcgt                                           25

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
tccgtctact gcgtcttcgt ctctt                                           25

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
gtatggcgga gaaataccaa caac                                            24

<210> SEQ ID NO 8
<211> LENGTH: 25
<212> TYPE: DNA
<213> ORGANISM: Artificial Sequence
<220> FEATURE:
<223> OTHER INFORMATION: Primer
```

<400> SEQUENCE: 8
ttgtatggtg gtctgctggg tagac                                      25

<210> SEQ ID NO 9
<211> LENGTH: 119
<212> TYPE: DNA
<213> ORGANISM: Artificial Sequence
<220> FEATURE:
<223> OTHER INFORMATION: Synthetic IHHNV template

<400> SEQUENCE: 9
cattctaccg tggtgcttca tagggaacag acccgtttct ctactgcctc tgcaacgagt    60
gttttataga caatctcaat gtcaacggac agtgtctaca ctgtcatccc gacgacgaa 119

<210> SEQ ID NO 10
<211> LENGTH: 100
<212> TYPE: DNA
<213> ORGANISM: Artificial Sequence
<220> FEATURE:
<223> OTHER INFORMATION: Synthetic IHHNV template

<400> SEQUENCE: 10
gatcctaagg tctgcgtgga taacctggga attcgagagg gaacaggaaa cggaacaatt 60
caacttggaa gtgaatcaga aacctccctt ggaagtgttg 100

<210> SEQ ID NO 11
<211> LENGTH: 108
<212> TYPE: DNA
<213> ORGANISM: Artificial Sequence
<220> FEATURE:
<223> OTHER INFORMATION: Synthetic IHHNV template

<400> SEQUENCE: 11
agatacggta ttgaacggct ttcgtatttt ggtcttggcc acgccatttt taaacgaatc 60
atcaaatact tccaacaata cagaagagac gaagacgcag tagacgga 108

<210> SEQ ID NO 12
<211> LENGTH: 116
<212> TYPE: DNA
<213> ORGANISM: Artificial Sequence
<220> FEATURE:
<223> OTHER INFORMATION: Synthetic IHHNV template

<400> SEQUENCE: 12
gtatggcgga gaaataccaa caaccggacc caccttcatc ccaaaatggg gtggtcaatt 60
aaaatgggac aaaccatccc ttggaaacct agtctaccca gcagaccacc atacaa 116

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
cgaaaccttc aacacacccg c 21

<210> SEQ ID NO 14
<211> LENGTH: 22
<212> TYPE: DNA
<213> ORGANISM: Artificial Sequence
<220> FEATURE:
<223> OTHER INFORMATION: Primer -continued

<400> SEQUENCE: 14
cggtggtggt gaaggagtag cc                                              22

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gtcctcctta ctgaggctcc c                                               21

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
gaggtcacga ccagccaagt cg                                              22

<210> SEQ ID NO 17
<211> LENGTH: 16
<212> TYPE: DNA
<213> ORGANISM: Artificial Sequence
<220> FEATURE:
<223> OTHER INFORMATION: Fluorescently labeled DNA probe
<220> FEATURE:
<221> NAME/KEY: misc_feature
<222> LOCATION: (1)..(1)
<223> OTHER INFORMATION: Labeled with FAM
<220> FEATURE:
<221> NAME/KEY: misc_feature
<222> LOCATION: (16)..(16)
<223> OTHER INFORMATION: Labeled with MGB

<400> SEQUENCE: 17
acccaccttc atccca                                                     16

<210> SEQ ID NO 18
<211> LENGTH: 25
<212> TYPE: DNA
<213> ORGANISM: Artificial Sequence
<220> FEATURE:
<223> OTHER INFORMATION: Fluorescently labeled DNA probe
<220> FEATURE:
<221> NAME/KEY: misc_feature
<222> LOCATION: (1)..(1)
<223> OTHER INFORMATION: Labeled with FAM
<220> FEATURE:
<221> NAME/KEY: misc_feature
<222> LOCATION: (25)..(25)
<223> OTHER INFORMATION: Labeled with TAMRA

<400> SEQUENCE: 18
tgggacaaac catcccttgg aaacc                                           25